United States Patent [19]

Devant

[11] Patent Number: 4,952,696

[45] Date of Patent: Aug. 28, 1990

[54] PROCESS FOR RESOLVING THE ENANTIOMERS OF A BENZOPYRAN DERIVATIVE

[75] Inventor: Ralf M. Devant, Darmstadt-Arheilgen, Fed. Rep. of Germany

[73] Assignee: Merck Patent Gesellschaft mit Beschraenkter Haftung, Darmstadt, Fed. Rep. of Germany

[21] Appl. No.: 479,893

[22] Filed: Feb. 14, 1990

[30] Foreign Application Priority Data

Feb. 15, 1989 [DE] Fed. Rep. of Germany ....... 3904496

[51] Int. Cl.$^5$ ........................................... C07D 401/00
[52] U.S. Cl. ................................................. 546/269
[58] Field of Search ......................................... 546/269

[56] References Cited

U.S. PATENT DOCUMENTS 4,788,305 11/1988 Tessier et al. ....................... 546/269

FOREIGN PATENT DOCUMENTS 0273262 7/1988 European Pat. Off. ............ 546/269

*Primary Examiner*—John M. Ford
*Assistant Examiner*—Robert C. Whittenbaugh
*Attorney, Agent, or Firm*—Millen, White & Zelano

[57] ABSTRACT

The invention relates to a process for resolving the enantiomers of trans-3-hydroxy-3,4-dihydro-2,2-dimethyl-4-(2-oxo-1,2-dihydropyridin-1-yl)-2H -1-benzopyran-6-carbonitrile (I), characterized in that racemic I, together with a small amount of (−)-I [or (+)-I], is dissolved in an inert solvent or solvent mixture, the solution is seeded with (−)-I [or (+)-I], the (−)-I [or (+)-I] which has precipitated is isolated, further racemis I is dissolved in the filtrate, the mixture is seeded with (+)-I [or (−)-I], the (+)-I [or (−)-I] which has precipitated is isolated, and if desired this crystallization cycle is repeated once or several times.

12 Claims, No Drawings

PROCESS FOR RESOLVING THE ENANTIOMERS OF A BENZOPYRAN DERIVATIVE

SUMMARY OF THE INVENTION

The invention relates to a process for resolving the enantiomers of trans-3-hydroxy-3,4-dihydro-2,2-dimethyl-4-(2-oxo-1,2-dihydropyridin-1-yl)-2-H-1-benzopyran-6-carbonitrile [trans-2,2-dimethyl-4-(2-pyridon-1-yl)-6-cyano-chroman-3-ol; "I"].

Racemic I, a conglomerate of the two enantiomers, is known from DE-A-No. 36 44 094. Information from which compounds of a certain general formula, which also includes the compound I, can be resolved into their enantiomers by methods which are known per se is also to be found therein. However, closer experimental details on the preparation of the enantiomers (+)-I and (−)-I from I are not described therein.

It is possible to resolve I by derivatization with chiral reagents and subsequent fractional crystallization. In particular, I can be reacted with chiral isocyanates to give the corresponding urethanes, for example with (+)- or (−)-1-phenethyl isocyanate to give the corresponding 1-phenethylurethanes; these can then be subjected to fractional crystallization and the two diastereomers in each case obtained can then be hydrolyzed.

However, in practice these processes of chemical resolution of enantiomers have great disadvantages. Thus, expensive auxiliary reagents are required; the resolution. requires two additional chemical reactions The invention is based on the object of providing a process for resolving the enantiomers of I, which has the disadvantages of these processes to only a minor degree, if at all.

Upon further study of the specification and appended claims, further objects and advantages of this invention will become apparent to those skilled in the art.

These objects are achieved by the discovery of the present process of "crystallization by entrainment".

The invention accordingly relates to a process for resolving the enantiomers of I, characterized in that racemic I, together with a small amount of (−)-I [or (+)-I], is dissolved in an inert solvent or solvent mixture, the solution is seeded with (−)-I [or (+)-I], the (−)-I [or (+)-] which has precipitated is isolated, further racemic I is dissolved in the filtrate, the mixture is seeded with (+)-I [or (−)-I], the (+)-I [or (−)-I] which has precipitated is isolated, and if desired this crystallization cycle is repeated one or several times.

It is surprising that this entrainment process can be used successfully in the case of I. Resolutions of the enantiomers of related compounds, for example the 3-methyl derivative of I, were unsuccessful.

Suitable solvents are, preferably, mixtures of halogenated hydrocarbons, in particular methylene chloride, with lower alcohols containing 1–4 C atoms, in particular methanol, ethanol or isopropanol. Mixtures containing methylene chloride and ethanol in a volume ratio of 10:1 to 30:1, in particular 20:1, are preferred.

In detail, racemic I is dissolved together with about 1.5–2.5% by weight of (−)- or (+)-I, advantageously under the influence of heat, in a mixture of about 30–50 volumes (for example ml, based on 1 g of I) of methylene chloride and 1.5–2.5 volumes of ethanol, and the solution is cooled and seeded with about 0.1–0.3% by weight of pure (−)-I- [or (+)-I]. The (−)-I [or (+)-I] which has crystallized out is isolated and advantageously filtered off. A further amount of the racemate corresponding to the amount of enantiomer previously filtered off is advantageously added to the filtrate and the material added is dissolved under the influence of heat. Renewed cooling and seeding with (+)-I [or (−)-I], that is to say the other enantiomer, causes crystallization of (+)-I [or (−)-I], which is likewise isolated and advantageously filtered off. This crystallization cycle can be repeated once or several times, by dissolving further racemic I in the filtrate last obtained, crystallizing further (−)-I [or (+)-I] by cooling and seeding, dissolving racemic I again in the filtrate thereof, isolating further (−)-I [or (+)-I] by cooling and seeding, dissolving racemic I again in the filtrate thereof, isolating further (+)-I [or (−)-I] by cooling and seeding and so on.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Fed. Rep. of Germany No. P 39 04 496.3, filed Feb. 15, 1989, are hereby incorporated by reference.

EXAMPLE 49 g of racemic I and 1 g of pure (−)-I are dissolved in a boiling mixture of 2 l of methylene chloride and 100 ml of ethanol. The mixture is cooled to 20°, while stirring, and seeded with 100 mg of pure (−)-I. After 2 hours, 7 g of (−)-I are filtered off; optical purity 96% ee, enantiomeric excess.

7 g of racemic I are added to the mother liquor and are dissolved by boiling. After cooling to 20°, the mixture is seeded with 100 mg of pure (+)-I. After 2 hours, 6 g of (+)-I are filtered off; optical purity 93% ee.

The crystallization cycle can be repeated several times.

Products having an enantiomer purity of ≧99% ee are obtained by a further recrystallization of the resulting enantiomers from ethanol or methylene chloride/ethanol mixtures:

(−)-enantiomer, melting point 262°–263°; $[\alpha]_D^{20} -88.5°$ (c=1 in methanol)

(+)-enantiomer, melting point 262°–263°; $[\alpha]_D^{20} +87.8°$ (c=1 in methanol)

The optical purity is determined as follows:

2.5 mg of I are dissolved in 2 ml of dry tetrahydrofuran. After addition of 30 μl of 1,8-diazabicyclo[5,4,0]undec-7-ene and 10 μl of (R)-(+)-1-phenethyl isocyanate, the mixture is stirred at 20° C. for 2 hours and subsequently taken up in ethyl acetate and washed with NaHCO$_3$ solution and water. After drying and removal of the solvent, the diastereomers are analyzed by high performance liquid chromatography (column: Merck RP-18; mobile phase: water/acetonitrile 65:35).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

I claim:

1. A process for resolving the enantiomers of trans-3-hydroxy-3,4-dihydro-2,2-dimethyl-4-(2-oxo-1,2-dihydropyridin-1-yl)-2H-1-benzopyran-6-carbonitrile (I), comprising:
dissolving racemic I together with a small amount of either the enantiomer (−)-I or the enantiomer (+)-I in an inert solvent or solvent mixture;
seeding the resultant solution with the enantiomer employed in the previous step;
isolating the resultant precipitated enantiomer;
dissolving additional racemic I in said solution;
seeding said solution with the other enantiomer;
isolating the precipitated enantiomer; and
repeating the above steps one or more times.

2. A process according to claim 1, wherein said solvent mixture is a mixture of methylene chloride and a lower alcohol.

3. A process according to claim 2, wherein said lower alcohol is an alcohol containing 1-4 C atoms.

4. A process according to claim 1, wherein said solvent mixture is a mixture of methylene chloride and ethanol in a volumetric ratio of about 10:1 to 30:1.

5. A process according to claim 1, wherein said solvent mixture is a mixture of methylene chloride and ethanol in a volumetric ratio of about 20:1.

6. A process according to claim 1 wherein said solvent mixture is a mixture of a halogenated hydrocarbon and a $C_{1-4}$-alcohol.

7. A process according to claim 1, wherein, prior to seeding with the desired enantiomer, said solution is cooled.

8. A process according to claim 1, wherein racemic I is initially dissolved with about 1.5-2.5 wt. % of the desired enantiomer in a mixture of about 30-50 ml of methylene chloride per gram of racemic I and about 1.5-2.5 ml of ethanol per gram of racemic I.

9. A process according to claim 1 wherein said solution is seeded with about 0.1-0.3 wt. % of the desired enantiomer.

10. A process according to claim 1, wherein the amount of racemic I added following each isolation step corresponds approximately to the amount of enantiomer isolated.

11. A process for resolving the enantiomers of trans-3-hydroxy-3,4-dihydro-2,2-dimethyl-4-(2-oxo-1,2-dihydropyridin-1-yl)-2H-1-benzopyran-6-carbonitrile (I), comprising:
isolating either the (−)-I or (+)-I enantiomer from a solution of racemic I together with a small amount of the enantiomer to be isolated in an inert solvent or a solvent mixture wherein said solution has previously been seeded with the enantiomer to be isolated.

12. A process for resolving the enantiomers of trans-3-hydroxy-3,4-dihydro-2,2-dimethyl-4-(2-oxo-1,2-dihydropyridin-1-yl)-2H-1-benzopyran-6-carbonitrile (I), comprising:
(a) dissolving racemic I together with a small amount of either the (−)- enantiomer or (+)-enantiomer in an inert solvent or solvent mixture;
(b) seeding the solution of step (a) with the enantiomer employed in step (a);
(c) isolating the enantiomer which was used to seed the solution in step (b);
(d) adding additional racemic I to the solution; and
(e) repeating the cycle of steps (a)-(d) one or more times, alternating the enantiomer used in each cycle between the (+)-enantiomer and the (−)-enantiomer.

* * * * *